United States Patent [19]

DelGiorno et al.

[11] Patent Number: 4,805,455

[45] Date of Patent: Feb. 21, 1989

[54] MUSCLE TESTING APPARATUS AND METHOD

[75] Inventors: Daniel DelGiorno, Fort Salonga; Henry Medina, Melville; William R. Accolla, Sea Cliff, all of N.Y.

[73] Assignee: MYO-TECH Corp., Boca Raton, Fla.

[21] Appl. No.: 42,475

[22] Filed: Apr. 24, 1987

[51] Int. Cl.⁴ .............................................. A61B 5/22
[52] U.S. Cl. ..................................................... 73/379
[58] Field of Search .......................... 73/379, 380, 381

[56] References Cited

U.S. PATENT DOCUMENTS

| | | |
|---|---|---|
| 2,255,711 | 9/1941 | Noor . |
| 2,342,019 | 2/1944 | Solinski . |
| 2,590,055 | 3/1952 | Timmerman . |
| 2,644,334 | 7/1953 | Perry . |
| 2,680,967 | 6/1954 | Newman . |
| 2,860,514 | 11/1958 | Lauru . |
| 3,045,667 | 7/1962 | Sellner et al. . |
| 3,081,634 | 3/1963 | Blaszkowski . |
| 3,158,028 | 11/1964 | Chope . |
| 3,174,343 | 3/1965 | Kasulis . |
| 3,285,070 | 11/1966 | McDonough . |
| 3,297,021 | 1/1967 | Davis et al. . |
| 3,374,675 | 3/1968 | Keropian . |
| 3,375,717 | 4/1968 | Impellizzeri et al. . |
| 3,395,698 | 8/1968 | Morehouse . |
| 3,442,132 | 5/1969 | De Mare . |
| 3,465,592 | 9/1969 | Perrine . |
| 3,474,776 | 10/1969 | O'Brien . |
| 3,670,573 | 6/1972 | Kroemer . |
| 3,717,857 | 2/1973 | Evans . |
| 3,752,144 | 8/1973 | Weigle, Jr. . |
| 3,894,437 | 7/1975 | Hagy et al. . |
| 3,995,492 | 12/1976 | Clynes . |
| 4,114,449 | 9/1978 | Dikeman et al. . |
| 4,231,255 | 11/1980 | Haski et al. . |
| 4,236,528 | 12/1980 | Stanec et al. . |
| 4,307,608 | 12/1981 | Useldinger et al. . |
| 4,333,340 | 6/1982 | Elmeskog . |
| 4,375,674 | 3/1983 | Thornton . |
| 4,462,252 | 7/1984 | Smidt et al. . |
| 4,501,148 | 2/1985 | Nicholas et al. . |
| 4,534,557 | 8/1985 | Bigelow et al. . |
| 4,592,371 | 6/1986 | Pellicano et al. . |
| 4,614,479 | 9/1986 | Liu . |
| 4,702,108 | 10/1987 | Amundsen et al. ................... 73/379 |

FOREIGN PATENT DOCUMENTS 2912981 10/1980 Fed. Rep. of Germany .

OTHER PUBLICATIONS

R. H. Nathan, "A Dynamometer for Biomechanical Use" J. Biomed Eng. 1979, vol. 1, No. 2; Apr. pp. 83-88.

Primary Examiner—Charles A. Ruehl
Attorney, Agent, or Firm—Wolder, Gross & Yavner

[57] ABSTRACT

A method and apparatus for testing the strengths of muscles and muscle groups of a person. The apparatus comprises a support frame, a guide post, a support arm, and a force sensing device. The guide post is connected to the support frame such that the position of the guide post can be adjusted along the width of the support frame, and the support arm is connected to the guide post such that the position of the support arm can be adjusted along the height of the guide post. The force sensing device is connected to the support arm, and is provided to engage a body area of a person subjected to a force from a selected muscle or muscle group and to generate an initial signal, such as an elective voltage, in response to the force applied to the force sensing device. The initial signal from the force sensing device is processed, and a resultant signal, representing the force applied to the force sensing device, is displayed. The apparatus is well suited for, and the method of this invention includes the steps of, testing corresponding muscles or muscle groups, such as corresponding left and right muscles, and comparing those test results to show how these corresponding muscles or muscle groups compare in strength and endurance.

14 Claims, 10 Drawing Sheets

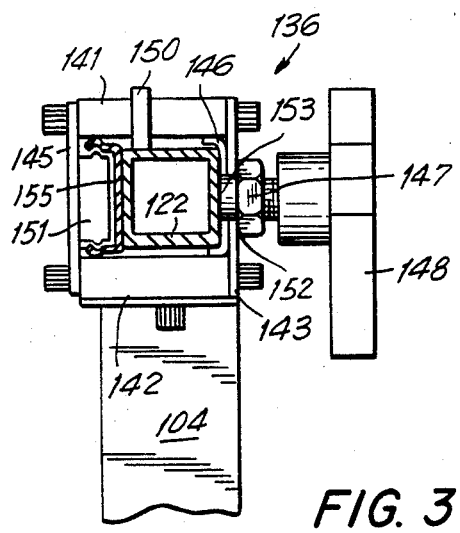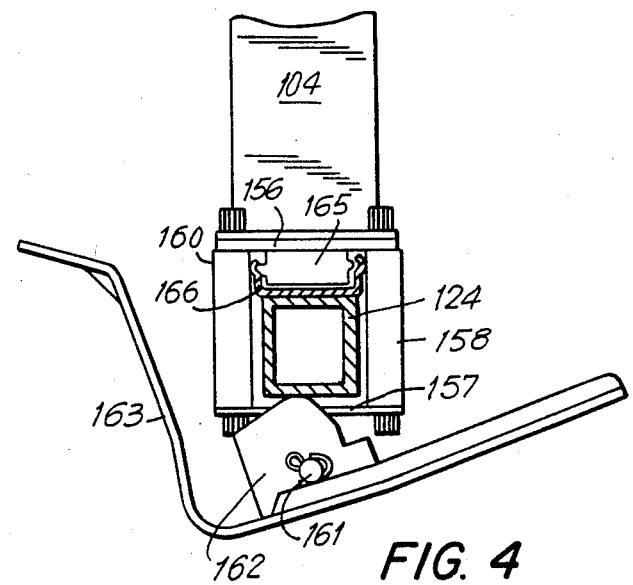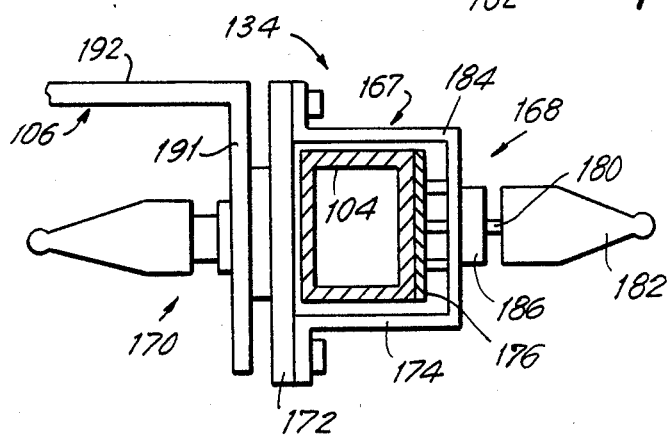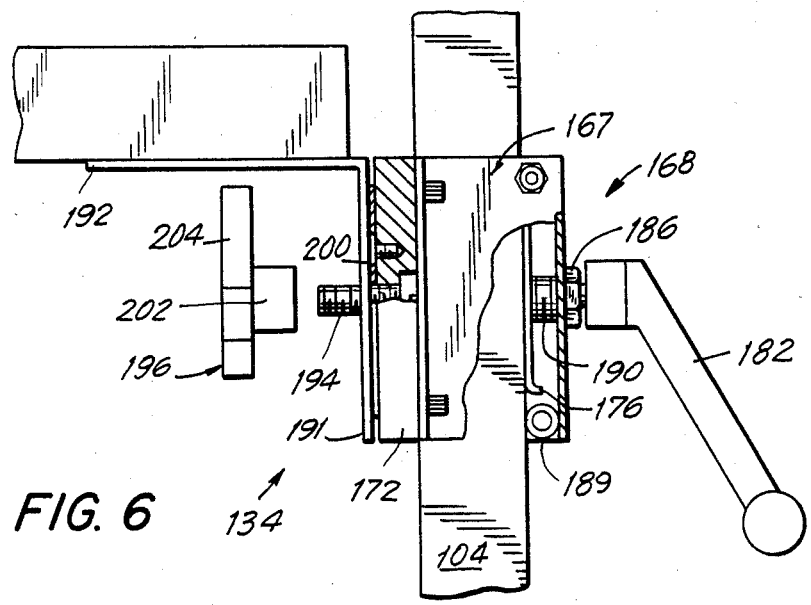

MUSCLE TESTING APPARATUS AND METHOD

BACKGROUND OF THE INVENTION

This invention generally relates to apparatus and methods for testing and indicating the strengths of muscles; and, more specifically, to apparatus and methods especially well-suited to test and indicate the strengths of individual muscles and the comparative strengths of corresponding muscles.

Recently, equipment has been developed to objectively and quantitatively measure the strength of individual muscles. As a therapeutic tool, such devices are very helpful in that they help a therapist identify specific muscles that need to be strengthened and to design a program that will help those particular muscles. Moreover, a quantitative measurement will tell not only which muscles are weak, but also how weak those muscles are. Further, as a person is undergoing treatment, an objective measure of the progress he or she is making, first, helps the therapist modify the treatment program, if necessary, and second, allows the patient to witness personally the fact that his or her muscles are getting stronger with therapy, which often encourages the patient to continue the treatment. In addition, often a patient may believe he or she is fully recovered and will discontinue treatment. An accurate, quantitative and objective measure of the strength of each muscle may show otherwise, however, and convince the patient to continue treatment.

As an exercise training tool, an objective and quantitative measurement of the strength of individual muscles will help a person or a trainer develop a highly personalized exercise program that concentrates on the muscles that need the most work. Occasional retesting will enable an individual to observe personally the progress he or she is making, and will help show how effective a particular exercise program is and, if it becomes advisable to do so, how a program should be modified. An individual may test and record the strengths of his or her muscles while healthy to provide a personal standard; and if that person is later injured, he or she, while recovering, can compare his or her muscle strengths against that recorded standard to determine whether the muscles have adequately recovered before resuming a particular activity, thus lessening the risk of a re-injury or of a new injury.

One prior art device for testing and indicating the strengths of individual muscles and muscle groups is disclosed in copending U.S. application Ser. No. 869,135, filed May 30, 1986. The apparatus disclosed in this copending application may be effectively employed to provide an objective and quantitative indication of the force developed by muscle over a period of time; nevertheless, it is believed that this prior art device may be improved upon in several respects. In particular, this prior art apparatus includes a pressure pad mounted on a horizontal support arm, that, in turn, is connected to a vertical guide post. The pressure pad is filled with a gas such as air and is connected to a transducer that generates an electric current in response to the pressure in the pressure pad. In use, a subject applies a force to the pressure pad, and the transducer then generates a current responsive to that force.

The pressure pad, though, is not movable along the length of the horizontal support arm, and the lateral position of the guide post is not readily adjustable, and the utility of the prior art device could be improved by increasing the maneuverability of the pressure pad and the guide post. Also, the current generated by the transducer is not linearly related to the force applied to the pressure pad, and this limits the usefulness of that current. In addition, the prior art apparatus is not specifically designed to automatically produce a permanent copy of the indication of the force developed by the muscle, or to automatically provide a display comparing one test result with another.

SUMMARY OF THE INVENTION

An object of the present invention is to support a force sensing means of a muscle testing apparatus so that the position of the force sensing means may be easily adjusted along at least two, and preferably three, mutually orthogonal, axes and yet is easy to hold rigidly in a multitude of positions relative to those axis.

Another object of this invention is to provide a muscle testing apparatus that produces an electric current linearly related to the force applied to a force sensing means of the apparatus.

A further object of the present invention is to test two different muscles or muscle groups, such as corresponding left and right muscles, of a subject and to provide an objective and quantitative comparison of those two tests.

Another object of the present invention is to provide a muscle testing apparatus that automatically compares two separate muscle tests and produces a paper copy showing that comparison.

These and other objectives are obtained with apparatus for testing the strengths of muscles and muscle groups of a person, and comprising a support frame, a guide post, a support arm, and force sensing means. First connecting means connects the guide post to the support frame; and this connecting means has a locked position wherein the guide post is rigidly connected to the support frame, and an unlocked positon wherein the guide post is supported by the support frame for sliding movement along a first axis. Second connecting means connects the support arm to the guide post; and this connecting means is adjustable between a locked position, wherein the support arm is rigidly connected to the guide post, and an unlocked position wherein the support arm is supported by the guide post for sliding movement along a second axis perpendicular to the first axis. Preferably, when the second connecting means is in its unlocked position, the support arm also may be pivoted about a horizontal unit.

The force sensing means is connected to the support arm to engage a body area of a person subjected to a force from a selected muscle or muscle group, and to generate an initial signal such as an electric current in response to the force applied to the sensing means. Procesing and display means is connected to the sensing means to receive the initial signal therefrom, to process that signal and to produce a resultant signal representing the force applied to the sensing means. Preferably, the apparatus also comprises third connecting means connecting the sensing means to the support arm and allowing the position of that sensing means to be adjusted along the length of the support arm.

In accordance with a second aspect of the present invention, a method is provided of comparing the strengths of first and second muscle groups of a subject. This method comprises the steps of stabilizing the subject's body, determining the range of motion of a first body area moved by the first muscle or muscle group, locating a force sensing means in that range, and contacting the force sensing means with that first body area. The first muscle or muscle group is than flexed to apply a first force against the sensing means for a first test period, and a selected parameter of that first force is measured. The method further comprises the steps of determining the range of motion of a second body area moved by the second muscle or muscle group, locating the force sensing means in the range of motion of that second body area, and contacting the force sensing means with that second body area. The second muscle or muscle group is then flexed to apply a second force against the sensing means for a second test period, a selected parameter of that second force is measured and a signal is displayed representing a comparison of the selected parameters of the first and second forces. The selected parameter may be, for example, the peak forces applied against the sensing means during the first and second test periods, or the integrals of the first and second forces over time. Preferably, this procedure is used to test and compare corresponding left and right muscles or muscle groups of a subject.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIGS. 3 and 4 are side views, partially in cross-section, showing further details of the apparatus of FIG. 1.

FIG. 5 is a top view, partially in cross-section, of several parts of the apparatus shown in FIG. 1, and in particular, showing the manner in which the support arm of the apparatus is connected to the guide post thereof.

FIG. 6 is a side view, partially in cross-section, of the assembly shown in FIG. 5.

DETAILED DESCRIPTION OF THE PREFERRED EMBODIMENTS

Figure 1:
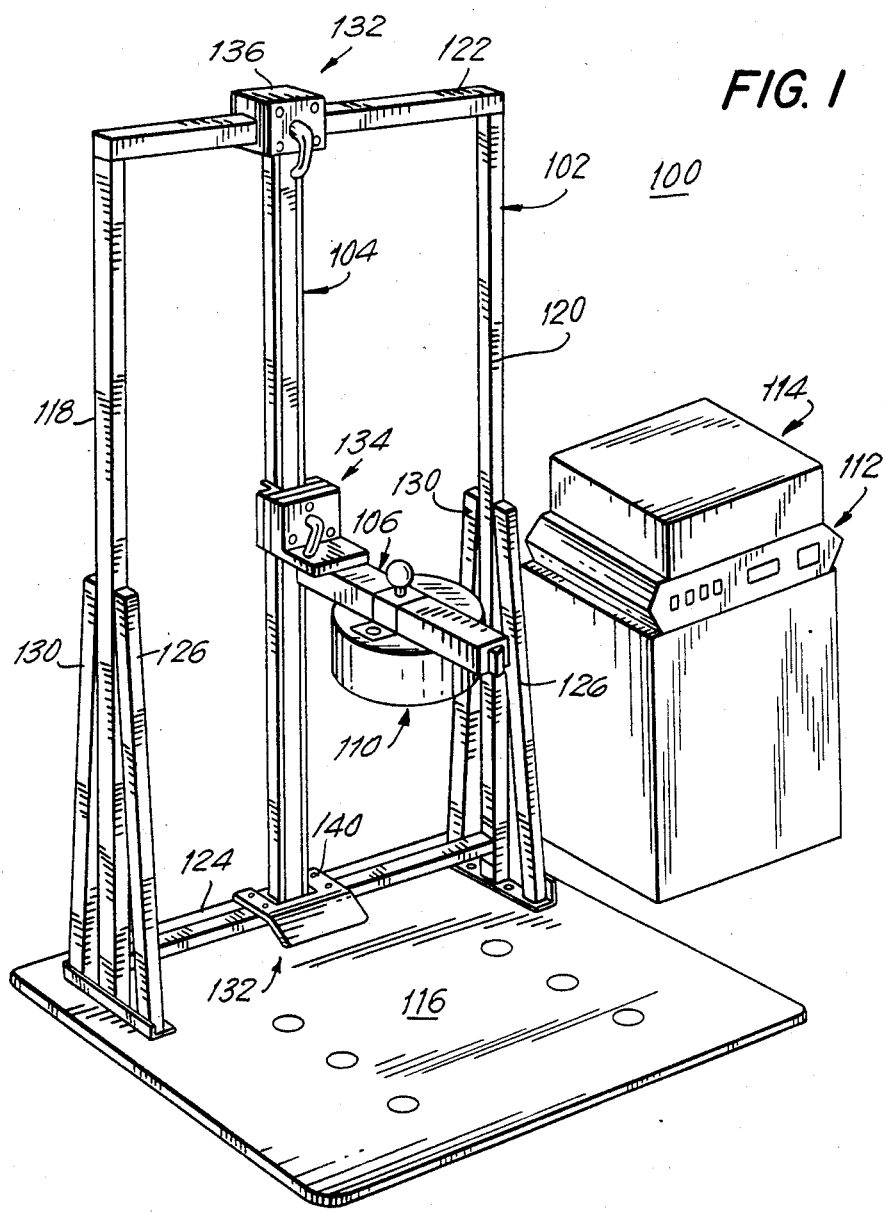
FIG. 1 is a front perspective view of an apparatus constructed in accordance with the present invention.
Figure 2:
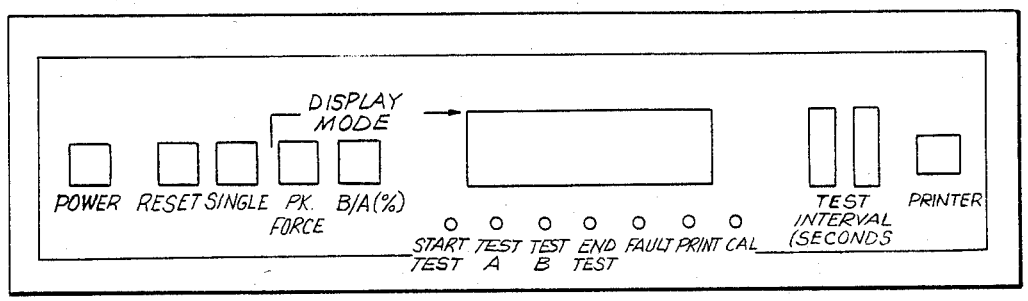
FIG. 2 is a front view of the processing means of the apparatus of FIG. 1.

FIG. 1 illustrates muscle testing apparatus 100 generally comprising support frame 102, guide post 104, support arm 16, sensing means 110, processing means 112 and display means 114. Support frame 102 supports guide post 104, support arm 106 and sensing means 110, and any suitable support frame may be used in the practice of the present invention. As shown in FIG. 1, support frame 102 includes base 116, left and right vertical posts 118 and 120, top and bottom horizontal bars 122 and 124, front brace legs 126, and back brace legs 130.

Base 116 has a flat, planar shape and rests on the floor, ground or other support surface, and posts 118 and 120 are secured to and extend upward from the base 116. Posts 118 and 120 generally define left and right sides of support frame 102, and legs 126 and 130 are connected to the posts to help support and stabilize those posts in upright positions. In particular, front legs 126 are connected to intermediate portions of posts 118 and 120, and the front legs slant forwardly downwardly therefrom and are connected to base 116; and back legs 130 are connected to mid-portions of posts 118 and 120, and the back legs slant rearwardly downwardly therefrom and are connected to base 116. Top bar 122 is connected to and horizontally extends between top ends of left and right posts 118 and 120, and bottom bar 124 is connected to and horizontally extends between bottom portions of the posts. The various parts of support frame 102 may be made of any suitable material such as stainless steel or chrome plated steel, and these parts may be connected together in any suitable manner to provide a strong, reliable support for guide post 104, support arm 106 and sensing means 110.

Guide post 104 is provided to support and guide movement of support arm 106 and sensing means 110, and for example the guide post may comprise a vertically extending post. Guide post 104 may be made from numerous materials and may have a variety of shapes and sizes, although preferably the guide post has a non-circular horizontal cross-section to help prevent support arm 106 from pivoting or swinging around the guide post. The embodiment of guide post 104 shown in FIG. 1 is made from stainless steel and has a hollow, rectangular horizontal cross-sectional shape.

Connecting means 132 connects guide post 104 to support frame 102; and this connecting means is adjustable between a locked position, wherein guide post 104 is securely connected to support frame 102 and is rigidly held in a fixed position relative thereto, and an unlocked position, wherein the guide post is supported by the support frame for sliding movement along a first axis. Connecting means 134 connects support arm 106 to guide post 104; and this connecting means is adjustable between a locked position wherein support arm 106 is securely connected to the guide pot 104 and rigidly held in a fixed position relative thereto, and an unlocked position, wherein the support arm is supported by the guide post for sliding movement along a second axis, perpendicular to the first axis. Preferably, when connecting means 132 is in its unlocked position, guide post 104 is supported for horizontal sliding movement along support frame 102; and when connecting means 134 is in its unlocked position, support arm 106 is supported for vertical sliding movement along guide post 104. In addition, when connecting means 134 is in its unlocked position, it also supports arm 106 for pivotal or rotary movement about a horizontal axis.

With the embodiments of the invention shown in FIG. 1, connecting means 132 includes upper connecting assembly 136 that connects guide post 104 to top bar 122, and lower connecting assembly 140 that connects the guide post to bottom bar 124, and FIGS. 3 and 4 show these connecting assemblies in greater detail. As shown in FIG. 3, upper connecting assembly 136 includes upper and lower plates 141, and 142, front and back plates 143 and 145, pressure plate 146 and locking screw 147; and preferably the upper connecting assembly further includes screw handle 148, at least one to roller 150, and guide member 151. Upper and lower plates 141 and 142 and front and back plates 143 and 145 are connected together to form a rectangular or square frame mounted on and encircling top bar 122, and a top end of guide post 104 is connected to lower plate 142 for movement therewith along the top bar. Guide post 104 may be connected to lower plate 142 in any suitable manner, and for example the top end of the guide post may be provided with a horizontal flange bolted to lower plate 142.

Pressure plate 146 is located inside the frame formed by plates 141, 142, 143 and 145, and is supported for sliding movement toward and away from top bar 122; and locking screw 147 extends through front plate 143, engages pressure plate 146, and is supported to move the pressure plate toward and away from top bar 122. More specifically, nut 152 is fixed on front plate 143, and screw 147 is threaded through this nut and extends through plate 143. An end of screw 147 is connected to a projection 153 fixed on plate 146 for forward and rearward movement therewith. Upper connecting assembly 136 is locked to top bar 122 by simply advancing screw 147 so as to advance plate 146 into a tight pressure engagement with the top bar, holding the entire upper connecting assembly rigidly in place; and upper connecting assembly 136 is unlocked by simply turning screw 147 so that it pulls pate 146 away from top bar 122, releasing the upper connecting assembly from that pressure engagement with the top bar.

Handle 148 is connected to screw 147 to help turn the screw; and one or more rollers 150 are rotatable supported by upper plate 141 and rest on top bar 122, supporting upper connecting assembly 136 on that bar and facilitating movement of the upper connecting assembly along the top bar. A guide bracket 155 having a c-shaped cross-section, is connected to the back side of top bar 122, with the open end of the guide bracket facing rearwardly. Guide member 151 is connected to an inside surface of back plate 145 and extends forward therefrom, into guide bracket 155, with upper and lower surfaces or edges of the guide member in a close yet sliding fit with the upper and lower legs of the guide bracket. In this way, bracket 155 and member 151 cooperate to guide movement of upper connecting assembly 136 along top bar 122 and help to insure that the upper connecting assembly and guide post 104 are held at the proper angular orientation relative to the top bar.

With reference to FIG. 4, lower connecting assembly 140 is similar to upper connecting assembly 136, and includes upper and lower plates 156 and 157 and front and back plates 158 and 160 connected together to form a square or rectangular frame mounted on and encircling bottom bar 124. A lower end of guide post 104 is connected to plate 156 in any suitable way for movement therewith along bottom bar 124, and for example the bottom end of the guide post may be provided with a horizontal flange connected to plate 156 by a plurality of bolts or screws.

Lower connecting assembly 140 further includes pivot rod 161, cam 162, pedal 163, and guide member 165. Rod 161 extends below bottom plate 157, parallel thereto and to bar 124, and the rod is connected to and is supported by plate 157 in any suitable manner. Pedal 163 is mounted on rod 161 for pivotal movement about the axis thereof, and cam 162 is connected to the pedal for pivotal movement therewith and into and out of engagement with lower bar 124. Pedal 163 is spring biased (by means not shown) toward the position shown in FIG. 4, where the pedal holds the top edge of cam 162 in tight pressure engagement with lower bar 124, holding the entire lower connecting assembly securely locked in place. Lower connecting assembly is unlocked by simply pivoting pedal 163 about rod 161 so as to move the upper edge of cam 162 away from bottom bar 124, releasing the lower connecting assembly from that pressure engagement with the bottom bar. Preferably, with reference to FIG. 1, pedal 163 is located so that a person standing on or adjacent apparatus 100 can use his or her foot to pivot pedal 163 to unlock lower connecting assembly 140 from bottom bar 124.

It should be noted that it is not necessary to connect cam 162 directly to pedal 163; and instead, for instance, the cam and pedal can both be rigidly connected to rod 161 for movement therewith about the axis of the rod and so that movement of the pedal is used to pivot the cam out of engagement with bar 124. Also, cam 162 may extend directly beneath lower plate 157, or the cam may be positioned laterally to a side of plate 157. If cam 162 extends directly beneath lower plate 157, then that plate includes an opening to allow the cam to extend upward through the plate and allow the necessary contact between the cam and plate 157.

A guide bracket 166 having a c-shaped cross-section is connected to the top side of bottom bar 124, with the open end of the guide bracket facing upwardly. Guide member 165 is connected to a bottom surface of plate 156 and extends downward therefrom, into guide bracket 166, with front and rear edges or surfaces of the guide member in a close yet sliding fit with the front and back legs of the guide bracket. With this arrangement, bracket 166 and guide member 165 cooperate to guide movement of lower connecting assembly 140 along bar 124 and help to hold the lower connecting assembly and guide post 104 at the proper angular orientation relative to bar 124.

FIGS. 5 and 6 illustrate connecting means 134 in greater detail; and, generally, this connecting means includes slide assembly 167 and first and second locking means 168 and 170. Slide assembly 167, in turn, includes front plate 172 and U-shaped bracket 174 connected together to form a hollow enclosure extending around the outside of guide post 104.

Locking means 168 adjustably connects slide assembly 164 to guide post 104; and this locking means 168 has a locked position securely holding slide assembly 167 in a fixed position on guide post 104, and an unlocked position wherein the slide assembly is slideable along the guide post. Preferably, this locking means 168 comprises pressure plate 176, threaded pin 180, and handle 182. Plate 176 is located inside slide assembly 167, between the slide assembly and the back of guide post 104, and the pressure plate is supported for movement toward and away from that guide post. For example, a plurality of guide pins 184 may be connected to pressure plate 176 and extend into bores in slide assembly 164 to support the pressure plate for movement toward and away from guide post 104.

Pin 180 is threaded through a nut 186 mounted on the back of bracket 174, rearward of pressure plate 176. Pin 180 extends rearward of slide assembly 164, and handle 182 is securely mounted on this rearward end of the threaded pin. To lock slide assembly 167 to guide post 104, handle 182 and pin 180 are turned so that the pin advances and pushes plate 176 into a tight, secure pressure engagement with guide post 104, holding the entire connecting means 134 in place. To unlock slide assembly 167, handle 182 and pin 180 are turned so that the pin moves rearward, releasing plate 176 from the pressure engagement with guide post 104, and allowing the slide assembly to slide along the guide post. A pair of rollers, one of which is shown at 189 in FIG. 6, may be connected to and supported by bracket 174, rearward of guide post 104, to guide and facilitate movement of slide assembly 167 along the guide post. Spring 190, shown in FIG. 6, may be disposed between pressure plate 176 and bracket 174 to urge the pressure plate into light engagement with guide post 104.

Support arm 106 extends away from slide assembly 167; and preferably, support arm 106 includes first and second legs 191 and 192. Legs 191 and 192 are connected together to form an L-shaped arm, with the former leg located immediately forward of slide assembly 167, and with the latter leg extending outward from leg 191, substantially perpendicular thereto. Locking means 170 adjustably connects support arm 106 to slide assembly 167, and this locking means 170 also has locked and unlocked positions. In its locked position, locking means 170 securely holds support arm 106 in a fixed position relative to slide assembly 167, and in its unlocked position, locking means 170 supports arms 106 for pivotal movement about a horizontal axis. This locking means 170 preferably includes threaded screw 194 and clamping means 196. Slide assembly 167 forms a front central, through opening 200, leg 191 of support arm 106 forms an aligned opening, and screw 194 extends through these aligned openings. The head of screw 194 abuts against an inside surface of slide assembly 167 to hold the screw against forward movement, and clamping means 196 is threadably mounted on the forward end of screw 194, forward of leg 191.

To lock support arm 106 to slide assembly 167, clamping means 196 is rotated to move it rearward on screw 194 (toward guide post 104) to securely and tightly clamp leg 191 against the slide assembly. To unlock support arm 106 from slide assembly 167, clamping means 196 is rotated to move it forward on screw 194 (away from guide post 104) to release leg 191 from the pressure engagement against the slide assembly. In this unlocked position, screw 194 still supports arm 106, and the arm may be pivoted about the axis of the screw.

Clamping means 196 preferably comprises threaded socket 202 mounted on screw 194, and handle 204 mounted on that socket. Handle 204 may be mounted on socket 202 by means of a pawl and a ratchet wheel so that the handle may be used to rotate the socket around screw 194 without requiring full rotation of the handle itself. A washer may be located between socket 202 and leg 191, and a clutch plate may be located between that leg and slide assembly 164.

Figure 7:
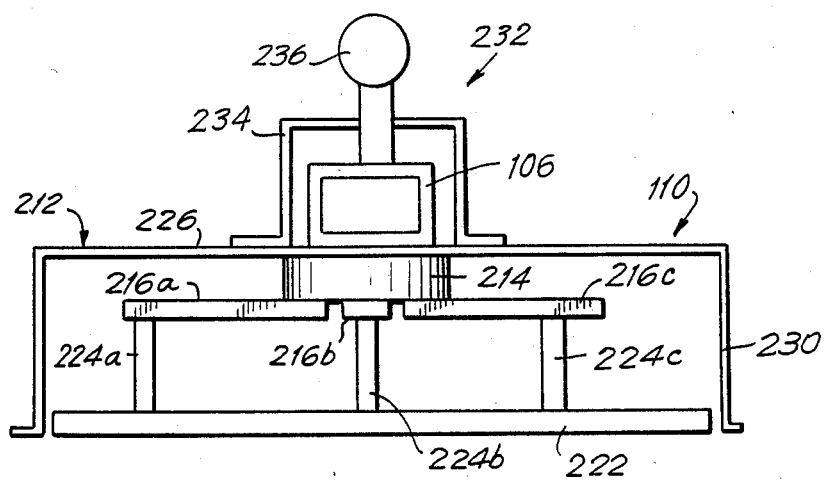
FIG. 7 is a front cross-sectional view showing the force sensing means of the apparatus illustrated in FIG. 1.
Figure 8:
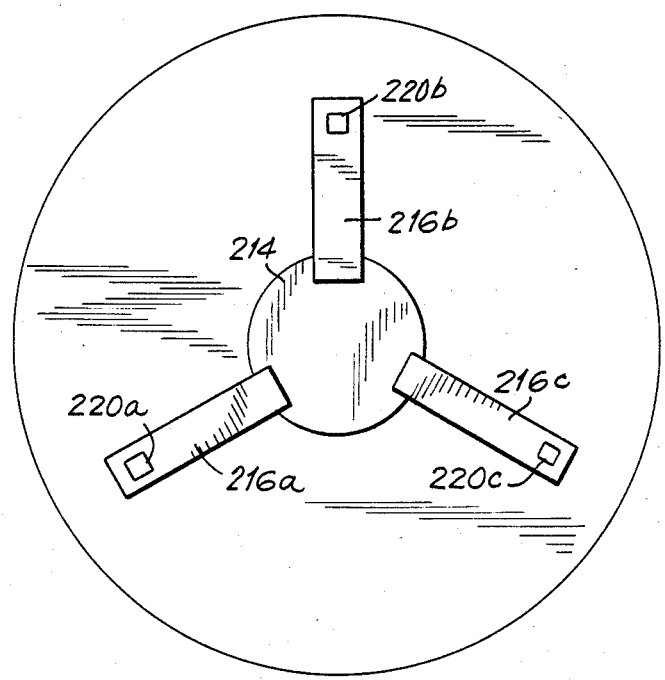
FIG. 8 is a bottom view of the force sensing means.

Sensing means 110 is connected to support arm 106 to engage a body area of a person subjected to a force from a selected muscle or muscle group, and to generate an initial signal, such as an electric current, in response to that force. With reference to FIGS. 1, 7 and 8, sensing means 110 preferably comprises housing or frame 212, base member 214, mounting bars 216a, b and c, strain gauges 220a, b and c, pressure plate 222, and connecting rods 224a, b and c. Housing 212 has a generally U-shaped vertical cross-section, including top, circular plate 226 and cylindrical side wall portion 230 extending outward therefrom, and base member 214 is connected to a central inside portion of top plate 226 and extends downward therefrom. Mounting bars 216a, b and c are connected to base member 214, and radially extend away from the axis of housing 212, coplanar with each other, and the mounting bars are circumferentially spaced apart 120°. Strain gauges 220a, b and c are mounted on the bottom sides of mounting bars 216a, b and c respectfully, and these gauges are positioned so that they are equidistant from the central axis of housing 212.

Pressure plate 22s has a substantially flat, circular shape, is located parallel to mounting bars 216a, b and c, and is connected thereto by threaded, rigid rods 224a, b and c. In particular, rod 224a is connected to plate 222 and to mounting bar 216a, rod 224b is connected to plate 222 and to mounting bar 216b, and rod 224c is connected to plate 222 and to mounting bar 216c. Preferably, rods 224a, b and c are parallel to each other and to the central axis of housing 212, and the rods are equidistant from that axis. A flexible cover (not shown) may be connected to the bottom edge of housing 212 and extend across the plate 222 to cover that plate and to enclose the inside of the housing.

In use, a subject applies a force to pressure plate 222 along an axis colinear with or parallel to the axis of housing 212. This force is transmitted to mounting bars 216a, b and c rods 224a, b and c, flexing those bars, and this changes the electrical resistance of strain gauges 220a, b and c. As explained in greater detail below, this change in electrical resistance is used to measure the force applied to pressure plate 222.

Preferably, sensing means 110 is connected to support arm 106 by means 232 allowing the position of the sensing means to be adjusted along the length of the support arm. With particular reference to FIGS. 1, 7 and 8, this connecting means 232 includes U-shaped clamp 234 and locking screw 236. Clamp 234 is mounted on support arm 106, with legs of the clamp securely connected to sensing means 110, on opposite sides of the support arm. Locking screw 236 is threaded through a base of clamp 234 and is supported thereby for movement toward and away from support arm 106. Clamp 234 and sensing means 110 may be locked to support arm 106 by turning screw 236 into a tight pressure engagement with support arm 106; and clamp 234 and sensing means 110 may be unlocked from support arm 106 by turning screw 236 so that it moves away from that pressure engagement with the support arm, allowing the clamp and sensing means to slide along the support arm.

Figure 9:
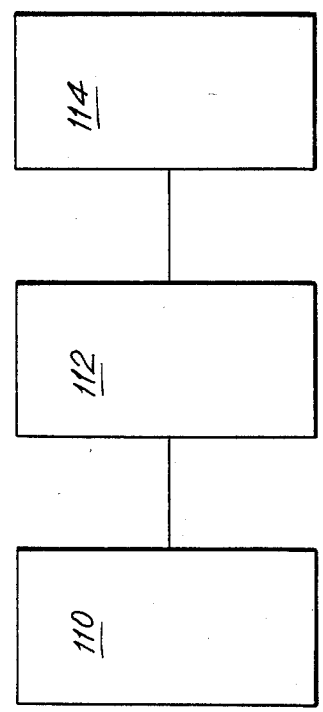
FIG. 9 is a simplified block diagram showing the relationship between the sensing means, the processing means, and the display means of the apparatus illustrated in FIG. 1.

Generally, as illustrated schematically in FIG. 9, processing and display means 112 and 114 are connected to sensing means 110 to receive the initial signal therefrom, to process that signal and to produce and display a resultant signal representing the force applied to the sensing means. As will be understood by those of ordinary skill the art, the signal from sensing means 110 may be processed in many different ways, numerous parameters representing the force applied to the sensing means may be shown on display means 114, and this display itself may take many forms.

For example, as described in greater detail below, the signal from sensing means 110 may be processed to determine the peak force applied to the sensing means during a particular test period, or to calculate the integral of the force applied to the sensing means over a particular test period. Display means 114 may be a printed controlled by processing means 112 to plot a chart or graph showing the force applied to sensing means 110 versus time for a test period, to print the peak force applied during the test period and to print the integral of the force applied to the sensing means over that test period. Display means 114 may also include a digital display, such as a four digit, seven segment liquid crystal display, that shows in real time either the force being applied to sensing means 110, or the integral of that force since the start of a test period.

Figure 10:
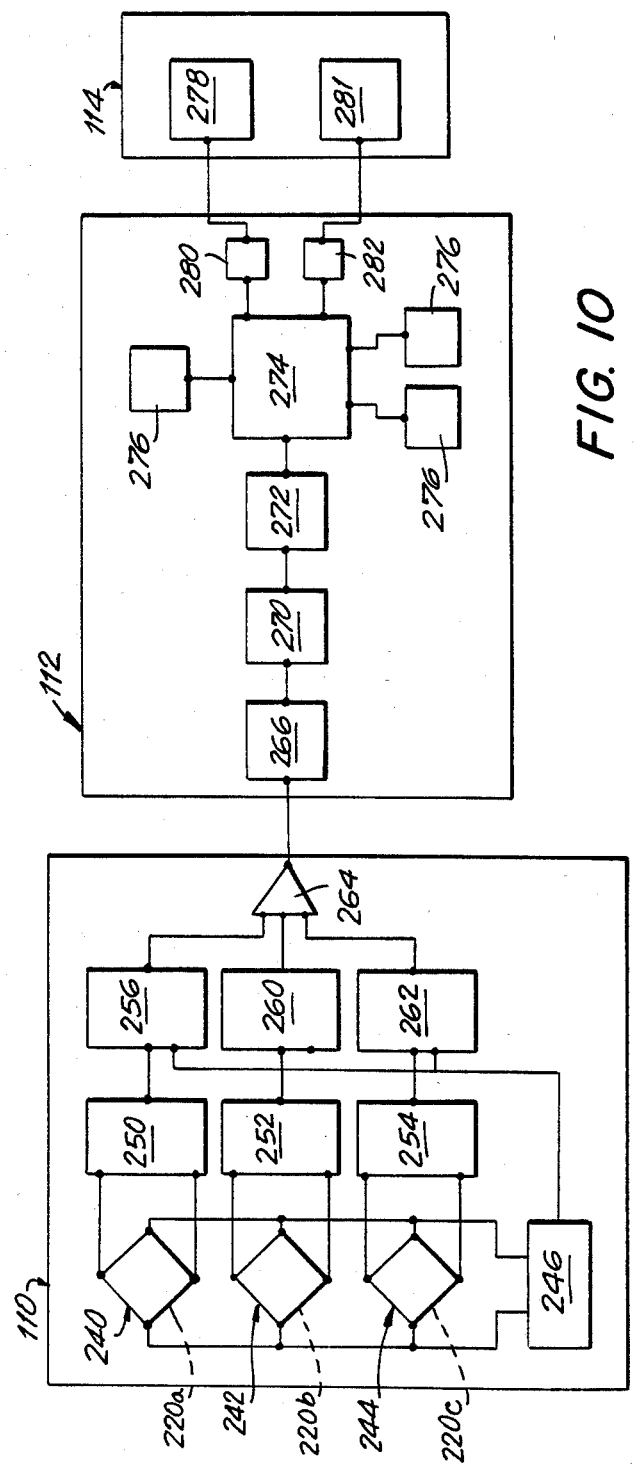
FIG. 10 is a more detailed schematic illustration of the sensing means, processing means and display means.

FIG. 10 is a schematic diagram showing sensing means 110, processing means 112 and display means 114 of apparatus 100 in greater detail. Sensing means 110 includes three Wheatstone bridges 240, 242 and 244, with each of the strain gauges 220$a$, $b$ and $c$ forming one leg of a different one of the bridges, and the resistances of the bridges are selected so that each bridge is balanced when the strain gauge of that bridge is in an unstressed state. Any suitable source of electric power 246 may be connected to the Wheatstone bridges 240, 242 and 244, although preferably that power source provides a pulsed voltage potential to decrease the power consumption of sensing means 110. By virtue of this arrangement, potential variations across each bridge 240, 242 and 244 will vary in accordance with changes in the resistance of the strain gauge of the bridge, which in turn will vary in accordance with the force applied to the bar 216$a$, $b$ or $c$, via pressure plate 222, on which the strain gauge is mounted.

The outputs of Wheatstone bridges 240, 242 and 244 are conducted respectively to signal conditioning means 250, 252 and 254, which amplify and stabilize the output currents of the Wheatstone bridges. The outputs of conditioning means 250, 252 and 254 are conducted respectively to rectifiers 256, 260 and 262, which are also powered by pulsed voltage source 246, to produce synchronized, rectified current signals. These signals from rectifiers 256, 260 and 262 are all conducted to summing amplifier 264, which sums the current applied thereto and amplifies that summed current, and the output of the summing amplifier is applied to signal processsng means 112.

Because strain gauge 220$a$, $b$ and $c$ are spaced apart 120° inside sensing means 110, the sum of the electrical outputs of Wheatstone bridges 240, 242 and 244 is independent of the specific location on pressure plate 222 to which a subject applies a force. To elaborate, the change in the resistance of each strain gauge, due to the application of a force to pressure plate 222, is directly proportional to the product of two factors. The first of these factors is the magnitude of the force applied to the pressure plate. The second of these factors is the length, along the diameter of housing 212 passing through the strain gauge, of the projection of the line between the point of application of that force and the strain gauge.

Figure 11:
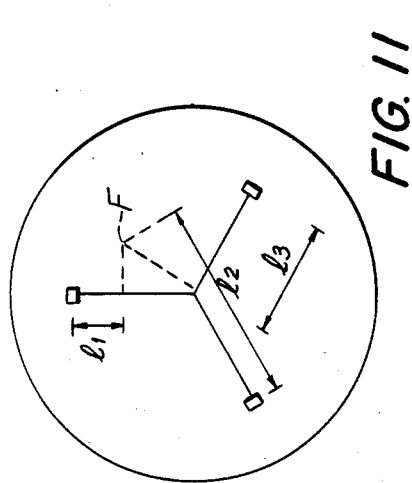
FIG. 11 is another bottom view of the force sensing means.

With particular reference to FIG. 11, the change in the resistance, $r_1$ of strain gauge 220$a$ is given by the equation $r_1 = Fl_1$, where F is the first of the above-defined factors, and $l_1$ is the second of the above-defined factors. Likewise, the changes in the resistances, $r_2$ and $r_3$, of strain gauges 220$b$ and $c$ are given by the equations: $r_2 = Fl_2$ and $r_3 = Fl_3$. Hence, the sum of the changes in the resistance, r, of strain gauges 220$a$, $b$ and $c$ is given by the equatin: $r = Fl_1 + Fl_2 + Fl_3 = F(l_1 + l_2 + l_3)$. As the point of application of force F moves around on pressure plate 222, elementary trigonometry shows that, while $l_1$, $l_2$ and $l_3$ may change individually, the sum $l_1 + l_2 + l_3$ remains constant. Hence, by virtue of the above-described arrangement, the output signal of amplifier 264 is both linearly related to the magnitude of the force applied to pressure plate 222 and independent of the specific point on the pressure plate to which that force is applied.

With reference again to FIG. 10, system processing means 112 preferably includes analog-to-digital converter 266, optical isolator 270, signal buffer 272, and microcomputer 274, and control section 276. The output of amplifier 264 is applied to converter 266, which, in a conventional manner, convert that signal to a digital representation of the force being applied to sensing means 110. For example, the output of converter 266 may be a series of on-off current pulses representing in binary form a number equal or related to the average magnitude of the force applied to pressure plate 222 over a very small increment of time.

The output of converter 266 is conducted across optical isolator 270, then to signal buffer 272, and thence to microcomputer 274. Optical isolator 270 is used to block the passage of high frequency signals to microcomputer 274, and this may be accomplish in various ways. For instance, the electrical current from converter 266 may be applied to a light emitting diode which blinks on and off in synchronization with the applied current. Light from this diode may be directed to an opto-responsive electrical element such as an optical transistor, which produces a pulsed electric current in synchronization with the blinking of the light emitting diode. The output of isolator 270 is conducted to buffer 272, which stabilizes and amplifies that output signal; and the output of buffer 272 is applied to microcomputer 274, which processes that signal in accordance with a preset program. Control section 276, which preferably is manually operated, is electrically connected to microcomputer 274, and is employed to set parameters used in the operation of apparatus 100 such as the length of a test period and various other values, discussed in detail below, needed to operate the microcomputer in the desired manner.

Microcomputer 274 may be programmed in various ways to process the signal applied thereto by means of many different routines. Preferably, microcomputer 274 generally operates in the following manner. During each test period, at frequent intervals, such as every 20 milliseconds, microcomputer 274 determines the force or average force being applied to pressure plate 222, and these values are stored in the computer memory. As a test is being performed, microcomputer 274 may operate liquid crystal display 278, via driver 280, to show, for example, a number representing the magnitude of the force being applied to pressure plate 222 or an integral of that force over time. After a test period is completed, microcomputer 274 is used to determined the peak force applied to pressure plate 222 during a test period and to integrate the force applied to the pressure plate over that period, and the microcomputer operates printer 281 via driver 282 to print these peak force and integral values. Microcomputer 274 also operates printer 281 to plot a chart or graph showing the force applied to the pressure plate versus time for a test period.

To test a particular muscle or muscle group of a subject, the subject is located in a stable position adjacent apparatus 100, and the range, or arc, of motion of a body area that is moved by a selected muscle or muscle group is determined. Sensing means 110 is positioned in that range of motion, preferably with the front face of pressure plate 222 perpendicular to the direction of the force developed by the muscle of muscle group. It is believed that the best results are obtained if pressure plate 222 is located at the middle of the arc, or range of motion, through which the body area would normally move as a result of the force applied to the body area by the muscle or muscle group being tested.

Sensing means 110 is located at a particular position by locking guide post 104 at a selected positioned along support frame 102, by locking support arm 106 at a selected height and angular orientatin along the guide post, and by locking the sensing means at a selected position along the support arm. An operator may wish to record these selected positions; and support frame 102, guide post 104, and support arm 106 are preferably provided with markings to indicate these positions. Also, a graph or chart may be located on base 116 of support frame 102, or on the floor adjacent apparatus 100 so that the operator can record the subject's position relative to the apparatus.

In addition, it is desirable to position the subject and sensing means 110 so that the muscle or muscle group being tested is isolated; that is, so that only forces developed by the muscle or muscle group being tested are applied to the sensing means. To accomplish this, when testing certain muscles or muscle groups, it may be preferred to have the patient sit in a chair with his or her legs raised off the ground or floor. A multitude of specific test positions and procedures with which apparatus 100 may be used are described in copending application Ser. No. 884,718, filed July 11, 1986.

With the subject and sensing means 110 properly positioned, the subject then contacts the sensing means with the body area and flexes the selected muscle or muscle group to force the body areea against the sensing means. The results of this test may then be displayed on display 114.

Figure 12A:
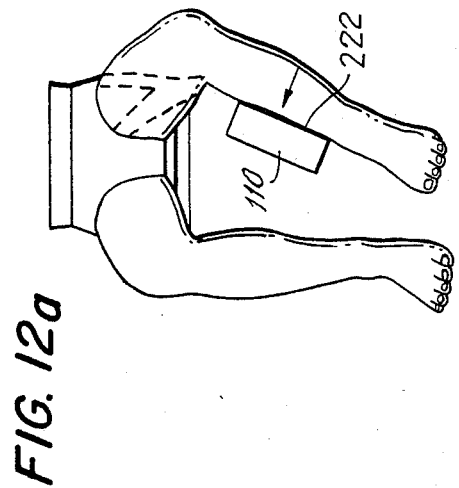
FIGS. 12a-f show positions of a subject and of the force sensing means of the apparatus of FIG. 1 to test six different muscles or muscle groups of the subject.

FIGS. 12a–f specifically illustrate the positions of a subject and sensing means 110 to test six different muscles or muscle groups. In particular, the positions of sensing means 110 and the subject to test the left sartorius and gracilus muscles are shown in FIG. 12a. The sensing means is located between the legs of the subject, with plate 222 facing the left leg and at an angle of about 25° to the vertical. The subject engages the pressure plate 222 with the inside of the lower part of the left leg, about midway between the left ankle and the knee, and flexes the left sartorius and gracilus muscles to apply an upward and inward force on the pressure plate.

Figure 12B:
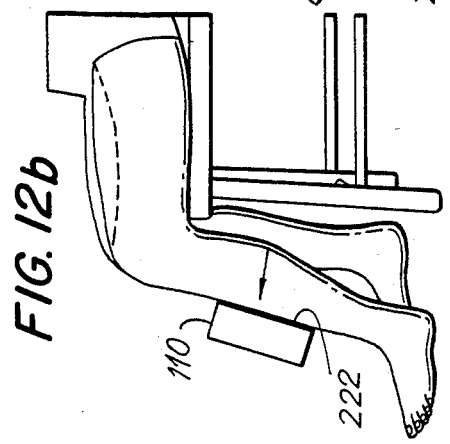

FIG. 12b shows the positions of the sensing means 110 and the subject to test the left quadriceps. The sensing means is located directly in front of the lower part of the left leg, with plate 222 toward that leg and at an angle of about 12° to 15° to the vertical. The subject engages plate 222 with the front of the lower part of the leg, about midway between the left knee and ankle, and flexes the left quadriceps to apply a forward and upward force on the pressure pad.

Figure 12C:
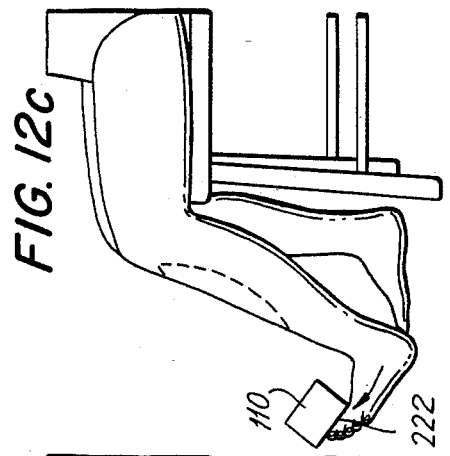

FIG. 12c shows the positions of the sensing means and the subject to test the left anterior tibial muscle. The sensing means is located directly forward of the left leg, with plate 222 facing downward and at an angle of about 25° to 30° to the horizontal. The subject pivots the lower part of the left leg forward slightly, contacts the sensing means with the top of the left foot, and flexes the anterior tibial muscle to apply an upward and rearward force on the sensing means. Preferably, care is taken to prevent the subject from flexing the thigh muscles or from raising the thighs to develop additional forces on the sensing means.

FIGS. 12a, b and c show procedures for testing muscles on the left side of the body; and, as will be understood, analogous procedures may be used to test the right sartorius and gracilus muscles, the right quadriceps, and the right anterior tibial muscle.

Figure 12D:
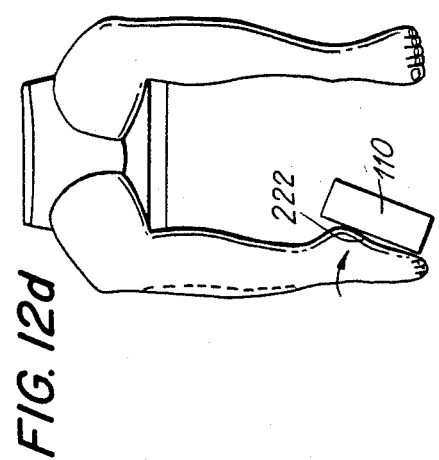

FIG. 12d shows the positions of the sensing means and the subject to test the right peroneus longus and peroneus brevis muscles. The sensing means is located between the legs of the subject at about the level of and adjacent the subject's right foot, with the pressure plate 222 facing outward toward the right leg and at an angle of about 30° to the vertical. The subject engages plate 222 with the bottom of the right foot, preferably with the left side of the bottom of that foot, and flexes his or her right peroneus longus and peroneus brevis muscles to apply a downward and laterally inward force on the pressure plate. Of course, an analogous procedure may be used to test the left peroneus longus and peroneus brevis muscles.

With the procedures illustrated in FIGS. 12a–d, it is preferred to have the subject seated in a chair with his or her legs and feet held relaxed, above the ground or floor, and it is desirable to hold the subject firmly in the chair by a seat belt or strap anchored or connected to the chair and extending across the front of the subject's waist or hips.

Figure 12E:
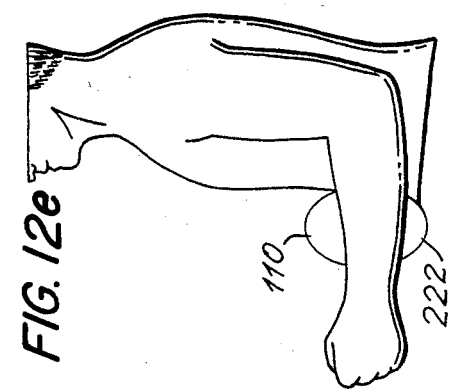

FIG. 12e illustrates the positions of the sensing means and the subject to test the left subscapularis muscle. The sensing means is located forward of and laterally slightly inward of the left arm, at about the height of the left elbow, with the plate 222 substantially vertical and facing laterally directly outward. The subject raises the left forearm, and flexes the left subscapularis muscle to apply an inward force to the pressure plate. It is advantageous to keep the upper part of the left arm vertical during the procedure; and, of course, an analogous method may be employed to test the right subscapularis muscle.

Figure 12F:
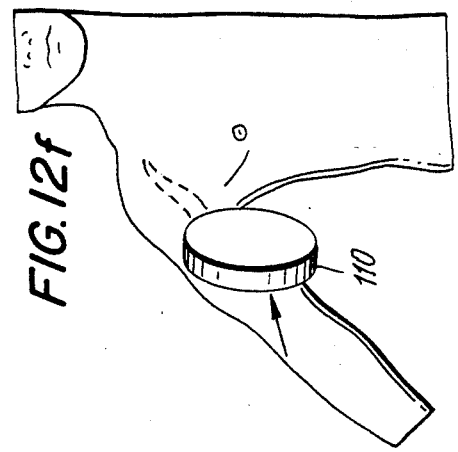

The positions of the sensing means and the subject to test the right coracobrachialis muscle are shown in FIG. 12f; and the sensing means is located forward of the subject and laterally outward of the right arm, with plate 222 facing laterally outward and slightly downward and rearward. The subject extends the right arm forwardly, downwardly and also slightly laterally outwardly, engages the pressure plate with an inside of the arm, and flexes the right coracobrachialis muscle to apply an upward and inward force to the pressure plate. Preferably, the pressure plate is located at a level slightly below the right shoulder, and the subject engages the plate with an inside of the upper part of the right arm, slightly above the elbow, and it is also desirable to have the subject keep the right forearm and the upper part of the right arm aligned, or straight, during this procedure. An analogous procedure may be used to test the left coracobrachialis muscle.

For the tests shown in FIGS. 12e and 12f, the subject may be seated or standing, although preferably the subject is seated in a chair with his or her legs and feet held relaxed, above the ground or floor. It is also preferred to hold the subject securely in the chair by a belt or strap anchored or connected to the chair and extending across the front of the subject's waist or hips.

Apparatus 100 is relatively simple to build and operate, and it is very easy for both the operator and the subject to understand and conduct the above-described testing procedures. The test results are immediately available, and are easy to read, understand and interpret. The test results are objective and consistent, minimizing human variables and other subjective factors that are inherent in manual muscle testing procedures. Because the test results are objective and consistent, they help an operator determine the accuracy of subjective complaints from a patient, and they help to diagnose basic problems. For instance, the test results show quantitatively how weak different muscles are, and help to distinguish between muscle weaknesses caused by nerve damage from muscle weaknesses caused by strain.

Figure 13:
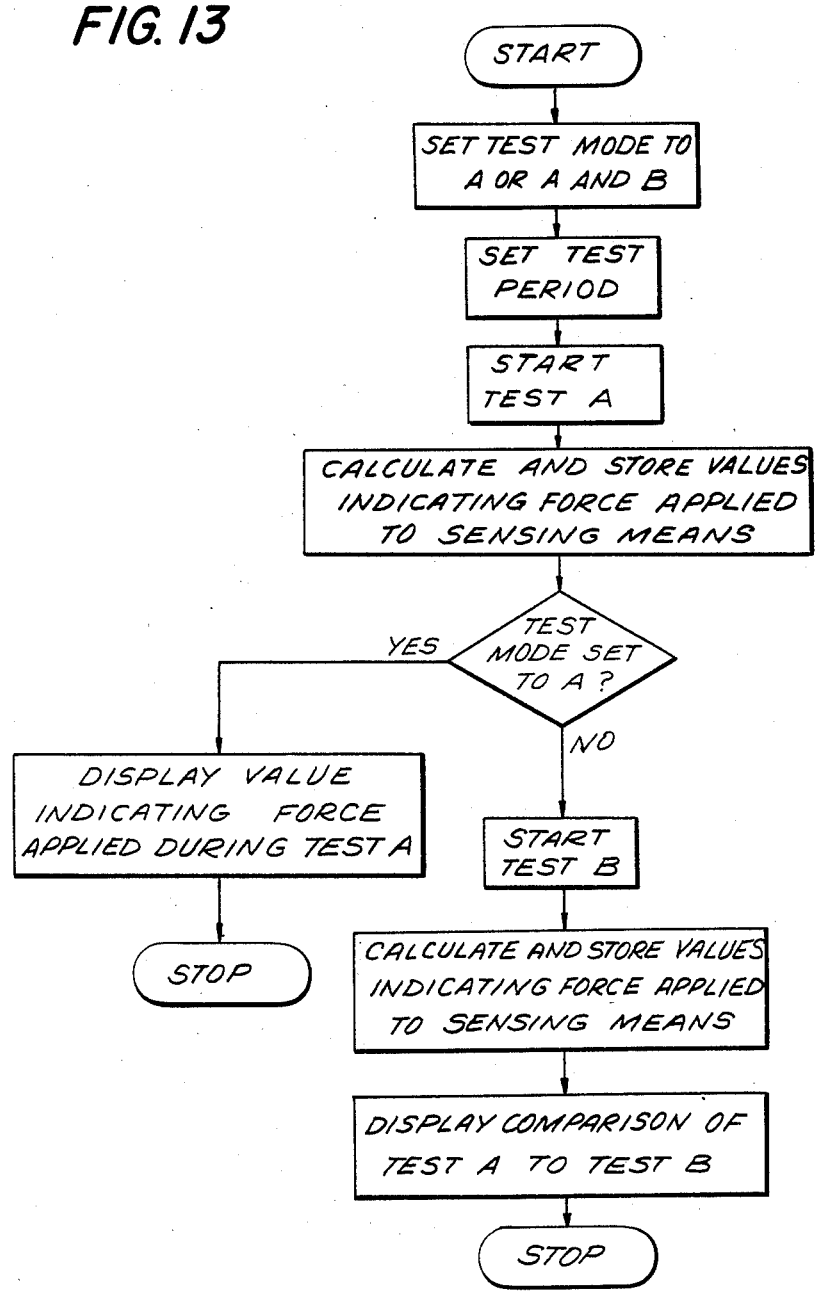
FIG. 13 is a flow chart illustrating one procedure for operating the apparatus of FIG. 1.

One particularly useful application for apparatus 100 is to test corresponding left and right muscles or muscle groups of a subject, and to compare those test results to show how these corresponding muscles or muscle groups compare in strength and endurance. Such a comparison is particularly helpful in diagnosing the extent of muscle damage due to injury or illness. FIG. 13 is a flow chart showing a procedure for testing either one muscle or muscle group or a pair of muscles or muscle groups. The first test, or the only test if only one test is performed, is referred to as test A, while the second test, if one is done, is referred to as test B. The first step in the procedure shown in FIG. 13 is to determine the test mode—that is, to determine whether only one or two tests will be conducted—and then to choose the length of the test period. After this, test A is performed. As outlined above, a first body area that is moved by a first selected muscle or muscle group is forced against sensing means 110, and microcomputer 274 is operated to store values representing one or more parameters of that force. If only one test is being done, when test A is completed, microcomputer 274 operates display 114 to produce an objective and quantitative indication of the force developed by the first selected muscle.

However, if two tests are being performed, then when test A is completed, test B is started. Using the same procedures discussed above, a second body area that is moved by a second selected muscle or muscle group is forced against sensing means 110, and microcomputer 274 is employed to store values representing one or more parameters of that force. Preferably, if the first selected muscle or muscle group is a left muscle or muscle group, then the second selected muscle or muscle group is the corresponding right muscle or muscle group, and vice versa. For instance, if test A is conducted to measure the strength of the left biceps, then test B is done to measure the strength of the right biceps. Likewise, if test A is performed to measure the strength of the right anterior tibial muscles, then test B is done to measure the strength of the left anterior tibial muscles.

Figure 14:
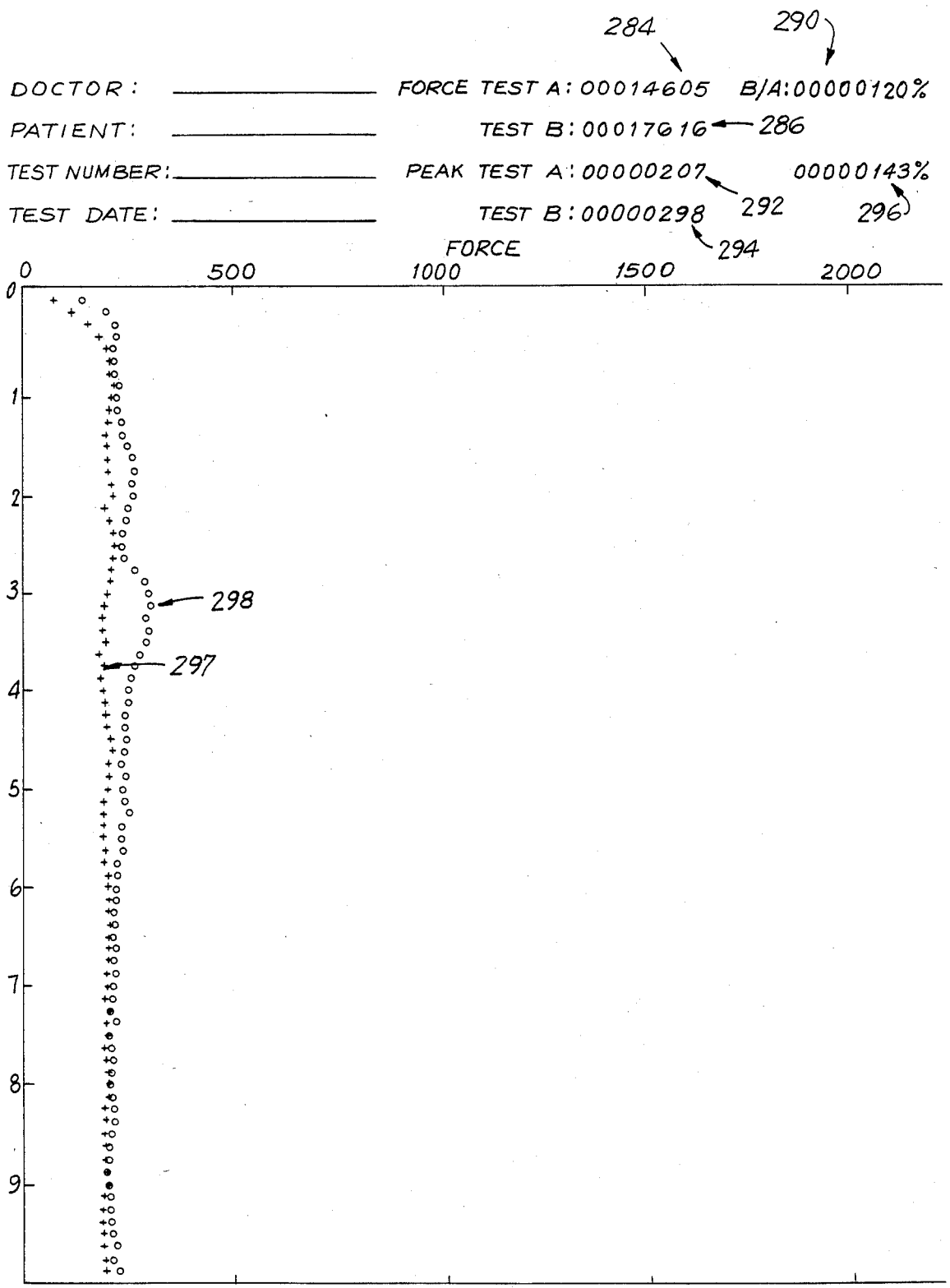
FIG. 14 shows the printed test results that may be obtained with the apparatus of FIG. 1.

After test B is completed, a selected parameter or parameters measured during test A is, or are, compared to a selected parameter or parameters measured during test B. For example, with reference to FIG. 14, a number, shown at 284, may be printed representing the integral of the force applied to sensing means 110 during test A, a second number, shown at 286, may be printed showing the integral of the force applied to the sensing means during test B, and a third number, shown at 290, may be printed to show the percent ratio of these two integrals. In addition, numbers representing or equal to the peak or maximum force applied to sensing means 110 during each of tests A and B, as well as a percent ratio of these peak value, may be printed. These latter values are shown at 292, 294 and 296 respectively in FIG. 14. FIG. 14 also includes graphs 297 and 298 showing the forces applied to the sensing means during tests A and B versus time, and these two graphs are superimposed over each other to better compare the results of the tests.

Figure 15:
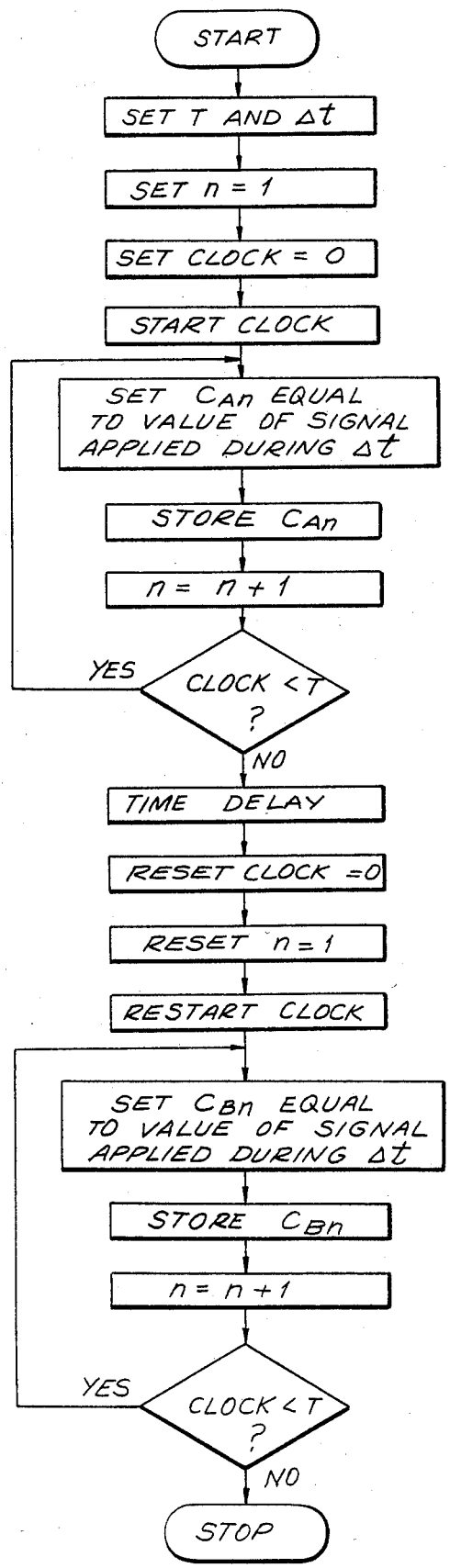
FIG. 15 is a simplified chart showing one procedure that may be used to operate the microcomputer of the apparatus of FIG. 1.

One program for the microcompuer 274 is illustrated in a simplified form in FIG. 15; and this program involves six variables identified as T, $\Delta t$, Clock, n, $C_{an}$ and $C_{bn}$. T is an externally controlled parameter that is set equal to the length of the test period, and $\Delta t$ is an externally or internally set parameter that simply establishes a basic unit of time, such as 20 milliseconds. Clock is an internal parameter that keeps track of the time that has elapsed since a test was started, and n is an internal counting variable that keeps track of the number of basic units of time that have elapsed since the start of a test period. $C_{an}$ is an internally set variable that is set equal to the value of the signal conducted to microcomputer 274 from converter 266 during the nth one of the basic units of time during test A, and $C_{bn}$ is an internally set variable that is set equal to the value of the signal conducted to microcomputer 274 from converter 266 during the nth one of the basic units of time during test B.

Various steps in the procedure shown in FIG. 15 are identified by number immediately to the left of the diagram. At the start of the program, the length of the test period, T, and the length of $\Delta t$ are chosen. $\Delta t$ may have a permanent value, or its value may be changed from one set of tests to another, although preferably $\Delta t$ and T are kept constant for any one set of tests. At step 2 in the program, n is set equal to one, and then the clock is set equal to zero and started. At step 5, $C_{an}$ is set equal to the value of the signal conducted to microcomputer 274 during the time interval $\Delta t$ and this value of $C_{an}$ is stored in the computer memory. Next, n is increased by one, and the clock is compared to T. If the time on the clock is less than T, the program returns to step 5, and the new $C_{an}$ is set equal to the value of the signal conducted to microcomputer 274 during the next time interval $\Delta t$. This value of $C_{an}$ is stored in the computer memory, n is again increased by one, and the clock is again compared to T. Steps 5 through 8 are repeated until the clock is equal to or greater than T, at which time, the program moves on to step 9.

Step 9 is a simple time delay, such as 3 or 5 minutes, which allows an operator to readjust the position of sensing means 110, if necessary, to prepare for test B. After this time delay, the clock is reset to zero and restarted and n is reset to one. $C_{bn}$ is set equal to the value of the signal conducted to microcomputer 274 during a unit of time $\Delta t$, and this value of $C_{bn}$ is stored in the computer memory. Then, n is increased by one, and the clock is compared to T. If the clock is less than T, the program loops back to step 13 and sets the new $C_{bn}$ equal to the value of the signal conducted to microcomputer 274 during the next basic time unit $\Delta t$. This value of $C_{bn}$ is stored in the computer memory, n is again increased by one, and the clock is again compared to T. Steps 13 through 16 are repeated until the clock is equal to or greater than T, at which time the program moves on to step 17, which ends the test routine.

Figure 16:
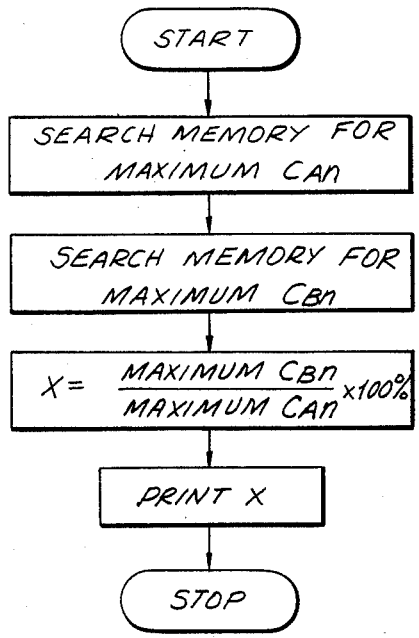
FIG. 16 is a simplified chart illustrating a procedure that may be used to display a comparison of peak forces applied to the force sensing means during two separate tests.

FIG. 16 is a flow chart illustrating in simplified form one procedure that may be followed to display the ratio of the peak force applied during test A to the peak force applied during peak B. At step 1 of this routine, the computer memory is searched for the maximum $C_{an}$; and at step 2, the memory is searched for the maximum $C_{bn}$. An internal variable X is then set equal to the ratio of a maximum $C_{bn}$ to the maximum $C_{an}$ times 100%, and then this variable is printed.

Figure 17:
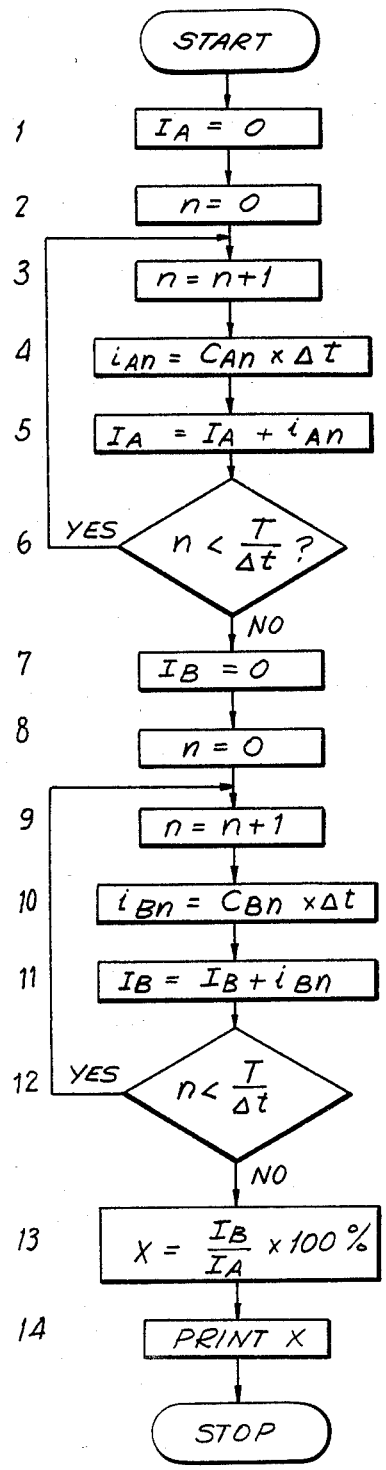
FIG. 17 is a simplified chart showing one procedure that may be used to display a comparison of the integrals of the forces applied to the muscle testing apparatus over two test periods.

FIG. 17 is a flow chart showing in simplified form one procedure that may be followed to display a comparison of the integrals of the forces applied to sensing means 110 during tests A and B. Generally, in accordance with this procedure, the integral of the force applied during test A is calculated by simply multiplying each $C_{an}$ value by $\Delta t$ and then adding all of these products; and, similarly, the integral of the force applied during test B is calculated by multiplying each $C_{bn}$ value by $\Delta t$ and then adding all of these products.

More specifically, at the start of the routine, variables $I_a$ and n are set equal to zero, and then n is increased by one. Then, a variable $i_{an}$, which represents the area under a part of the curve of the applied force during test A, is set equal to the product of $C_{an}$ and $\Delta t$, and $I_a$ is increased by this $i_{an}$. Then n is compared to $T/\Delta t$, which indicates the total number of basic units of time, $\Delta t$, that elapsed during the test period A. If n is less than or equal to $T/\Delta t$, the program returns to step 3, and n is increased by one, the new $i_{an}$ is calculated, $I_a$ is increased by the new $i_{an}$ and n is again compared to T divided by $\Delta t$. Steps 3 through 6 are repeated until n is greater than $T/\Delta t$; and when this occurs, $I_a$ is, for all practical purposes, equal to the integral of the force applied during test A over time, and the program moves on to step 7.

A variable $I_b$ is set equal to zero, and n is reset to zero. An internal variable $i_{bn}$, which represents the area under a part of the curve of the applied force during the test B, is set equal to the product of $C_{bn}$ and $\Delta t$, and $I_b$ is increased by $i_{bn}$. Then, n is compared to $T/\Delta t$, which indicates the number of basic units of time, $\Delta t$, that elapsed during test B. If n is not greater than $T/\Delta t$, the program loops back to step 9, n is increased by one, the new $i_{bn}$ is determined, $I_b$ is increased by the new $i_{bn}$, and n is again compared to $T/\Delta t$. Steps 9 through 12 are repeated until n is greater than $T/\Delta t$; and when this occurs, $I_b$ is, for all practical purposes, equal to the integral of the force applied during test B over time, and the program proceeds to step 13. An internal variable X is set equal to the ratio of $I_b$ to $I_a$ times 100 percent, and then X is printed.

Figure 18:
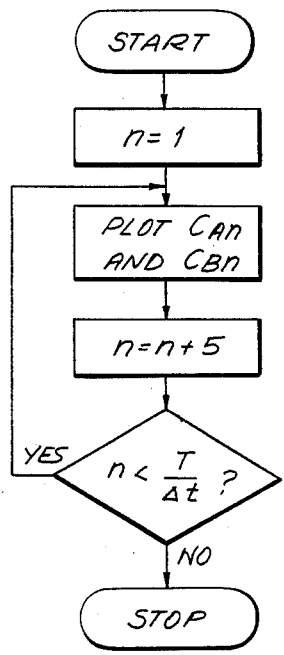
FIG. 18 is a chart showing a procedure that may be used to plot the forces applied to the muscle testing apparatus versus time for two different tests.

FIG. 18 illustrates in simplified form, one routine that may be followed to plot the forces applied during tests A and B versus time. With this routine, n is initially set equal to one, and $C_{an}$ and $C_{bn}$ are plotted on a graph, as shown in FIG. 14. For example, as shown in FIG. 14, an "o" may be printed on a graph at a distance from the time axis representing the value of $C_{an}$, and an "x" may be printed on the graph at a distance from the time-axis represent the value of $C_{bn}$. Then, n is increased by five, and n is compared to $T/\Delta t$. If n is not greater than $T/\Delta t$, the routine returns to step 2, new values of $C_{an}$ and $C_{bn}$ are plotted, n is again increased by five, and the new n is compared to $T/\Delta t$. Steps 2 through 4 are repeated until n is greater than $T/\Delta t$, at which time the program ends.

Figure 21:
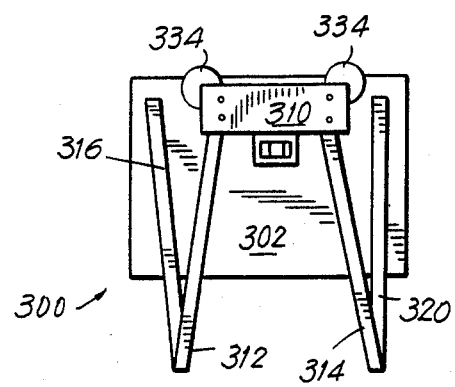
FIG. 21 shows the frame of FIGS. 19 and 20 in a collapsed or folded position.
Figure 20:
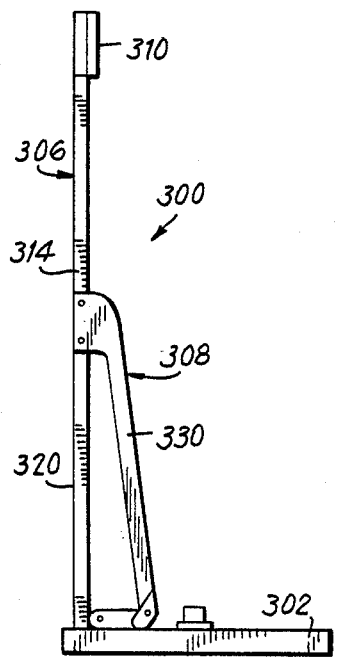
FIGS. 19 and 20 are front and side views respectively of an alternate support frame that may be used in the practice of this invention.
Figure 19:
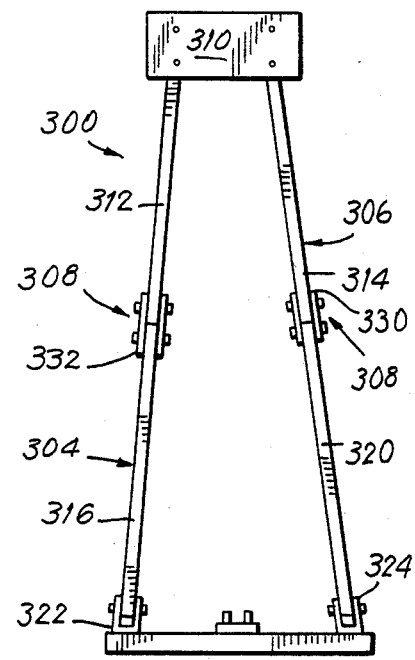

FIGS. 19–21 show a portable stand 300 that may be used in lieu of frame 102 to support guide post 104, support arm 106 and sensing means 110; and this stand 300, generally, includes base 302, left and right legs 304 and 306, locking means 308 and head plate 310. Each leg 304, 306, in turn, includes upper section 312, 314, lower section 316, 320, and lower hinge 322, 324. Preferably, locking means 308 include a pair of braces 330, 332, and stand 300 further includes a pair of wheels 334.

Base 302 has a generally flat, rectangular or square shape and is adapted to be placed on the ground, a floor or a similar support surface. Lower hinges 322, 324 connect lower sections of legs 304, 306 to base 302 for pivotal movement between a folded position (shown in FIG. 21) and an open position (shown in FIGS. 19 and 20). In their folded position, lower sections 316, 320 extend generally, and preferably substantially, parallel to base 302; and in their open position, lower sections 316, 320 extend upward from base 302, preferably substantially perpendicular thereto.

Middle hinges (not shown) connect upper leg sections 312, 314 to lower leg sections 316, 320 also for movement between a folded position (shown in FIG. 21) and an open position (shown in FIGS. 19 and 20). In their folded position, upper leg sections 312, 314 each forms an acute angle with the lower leg sections 316, 320 respectively, and preferably this acute angle is less than ten or fifteen degrees. In their open position, upper leg sections 312, 314 each are co-linear, or at least generally co-linear, with lower leg sections 316, 320 respectively.

With the above-described arrangement, each leg 304, 306 is moveable between a completely folded position (shown in FIG. 21) and a completely opened position (shown in FIGS. 19 and 20). In the completely folded position, the lower sections of the legs extends generally parallel to base 302, and the upper and lower sections of each leg form an acute angle. In the completely opened position, the lower sections of the legs extends upward from base 302, and the upper and lower sections of each leg are at least generally co-linear.

Locking means 308 is provided to hold legs 304, 306 in their completely opened positions. With the preferred locking means, each of a pair of braces 330, 332 is connected to base 302 for pivotal movement between a folded position wherein the brace is generally parallel to the base, and an open position wherein the brace extends upward from the base and engages both the upper and lower sections of one of the legs 304, 306. When legs 304, 306 are in their completely opened position, and braces 332 are in their open position, the braces may be securely connected to both the upper and lower sections of the legs in any suitable manner, such as by screws or bolts, to hold the legs rigid in their completely open position.

Head plate 310 extends between and is securely connected to upper sections of left and right legs 304 and 306, and preferably to top ends thereof. With stand 300 in its completely opened and locked position, shown in FIGS. 19 and 20, the stand provides a suitable support for guide post 104; and in particular, the top of guide post 104 may be connected to head plate 310, and the bottom of the guide post may be connected to base 302.

Preferably, guide post 104 is connected to stand 300 so that the guide post cannot move relative to the stand, and thus the guide post does not have the same lateral maneuverability it has when used with support frame 102. However, stand 300 itself is much more mobile than support frame 102, and may be easily moved from one location to another to support guide post 104, arm 106 and sensing means 110 in many different locations, for instance, to give field demonstrations of the muscle testing apparatus.

In order to help move stand 300 itself from one location to another, wheels 334 may be connected to base 302 in any suitable manner. Preferably, each wheel 334 is rotatable about its axis and projects beyond an edge of the base. To move stand 300, it is folded from the completely opened and locked position of FIGS. 19 and 20 to the completely folded position of FIG. 21. Stand 300 is positioned so that wheels 334 engage the ground or floor, and then the stand is simply rolled along that surface.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

What is claimed is:

1. Apparatus for testing the strengths of muscles and muscle groups of a person, comprising:
   a support frame including
   a left vertical support post,
   a right vertical support post,
   a top bar connected to and horizontally extending between the left and right vertical support post, and a bottom bar connected to and horizontally extending between the left and right vertical support post;
   a guide post;
   first connecting means connecting the guide post to the support frame, the first connecting means having a locked position wherein the guide post is rigidly connected to the support frame, and an unlocked position, wherein the guide post is supported by the support frame for horizontal sliding movement along the support frame along a first axis, said first connecting means including
   an upper connecting assembly connecting the guide post to the top bar and
   a lower connecting assembly connecting the guide post to the bottom bar;
   a support arm;
   second connecting means connecting the support arm to the guide post, the second connecting means having a locked position, wherein the support arm is rigidly connected to the guide post, and an unlocked position, wherein the support arm is supported by the guide post for vertical sliding movement along the guide post along a second axis, perpendicular to the first axis;
   sensing means connected to the support arm to engage a body area of the person subjected to a force from a selected muscle or muscle group, and to generate an initial signal in response to the force;
   third connecting means connecting the sensing means to the support arm, the third connecting means having a locked position, rigidly holding the sensing means in place on the support arm, and a slide unlocked position, wherein the sensing means is supported for sliding movement along a third axis along the support arm; and
   processing and display means connected to the sensing means to receive the initial signal therefrom, to process the initial signal and to produce and display a resultant signal representing said force.

2. Apparatus according to claim 1, wherein the third connecting means includes:
   a clamp mounted on the support arm and securely connected to the sensing means; and
   a locking screw threaded through the clamp and supported thereby for movement into and away from a tight pressure engagement with the support arm.

3. Apparatus according to clam 1, wherein the sensing means defines an axis and includes
   a base member;
   first, second and third bars connected to the base member,
   radially extending away from the axis of the sensing means, and circumferentially spaced apart 120°;
   first, second and third strain gages mounted on the first, second and third bars respectively;
   a pressure plate to engage the body area of the subject; and
   means connecting the pressure plate to the first, second and third bars to transmit forces from the pressure plate to the first, second and third bars.

4. The apparatus according to claim 1, wherein said third connecting means further has a pivoting unlocked position, wherein the sensing means is supported for rotation about said third axis.

5. A method of comparing the strengths of first and second selected muscles or muscle groups of a subject, comprising the steps of:
   stabilizing the subject's body;
   determining the range of motion of a first body area moved by the first selected muscle or muscle group;
   locating a force sensing means in said range;
   contacting the sensing means with the first body area;
   flexing the first selected muscle or muscle group to apply a first force against the sensing means for a first test period;
   measuring a selected parameter of the first force;
   determining the range of motion of a second body area moved by the second selected muscle or muscle group;
   locating the force sensing means in the range of motion of the second body area;
   contacting the sensing means with the second body area;
   flexing the second selected muscle or muscle group to apply a second force against the sensing means for a second test period;

measuring a selected parameter of the second force; and displaying a signal representing a comparison of the selected parameters of the first and second forces.

6. A method according to claim 5, wherein:
the selected parameter of the first force is the peak force applied against the sensing means during the first test period; and
the selected parameter of the second force is the peak force applied against the sensing means during the second test period.

7. A method according to clam 5, wherein:
the selected parameter of the first force is the integral of the first force over the first test period; and
the selected parameter of the second force is the integral of the second force over the second test period.

8. A method according to claim 5, wherein the first selected muscle or muscle group is a particular left muscle or muscle group, and the second selected muscle or muscle group is a right muscle or muscle group corresponding to said particular left muscle or muscle group.

9. A method of comparing the strengths of first and second selected muscles or muscle groups of a subject, and for use with apparatus including a support frame, a guide post connected to the support frame for selective horizontal sliding movement therealong, a support arm connected to the guide post for selective vertical sliding movement therealong and for selective pivotal movement about a horizontal axis, and sensing means connected to the support arm for selective sliding movement therealong, the method comprising the steps of:
stabilizing the subject's body adjacent the support frame;
determining the range of motion of a first body aea moved by the first selected muscle or muscle group;
locating in the force sensing means in said range, including the steps of
 (i) sliding the guide post along the support frame to a set horizontal position,
 (ii) locking the guide post in the set horizontal position,
 (iii) sliding the support arm along the guide post to a set height,
 (iv) pivoting the support arm about the horizontal axis to a set angular position,
 (v) locking the support arm in the set height and the set angular position,
 (vi) sliding the sensing means along the support arm to a set position therealong, and
 (vii) locking the sensing means to the support arm in the set position therealong;
contacting the sensing means with the first body area;
flexing the first selected muscle or muscle group to apply a first force against the sensing means for a first test period;
measuring the first force applied against the sensing means during the first test period, including the steps of
 (i) generating an electric voltage signal representing the magnitude of the force applied to the sensing means,
 (ii) dividing the first test period into a multitude of equal first time intervals,
 (iii) during each of the first time intervals, establishing a number representing the magnitude of the electric voltage signal during the first time interval, and
 (iv) storing in a first memory all of the numbers established during the first test period;
determining the range of motion of a second body area moved by the second selected muscle or muscle group;
locating the force sensing means in the range of motion of the second body area;
contacting the sensing means with the second body area;
flexing the second selected muscle or muscle group to apply a second force against the sensing means for a second test period;
measuring the force applied to the sensing means during the second test period, including the steps of
 (i) generating an electric voltage signal representing the magnitude of the force applied to the sensing means during the second test period,
 (ii) dividing the second test period into a multitude of equal second time intervals,
 (iii) during each of the second time intervals, establishing a number representing the magnitude of the electric voltage signal during the second time interval, and
 (iv) storing in a second memory all of the numbers established during the second test period; and
displaying a signal representing a comparison of the forces applied to the sensing means during the first and second test periods.

10. A method according to claim 9, further including the steps of:
recording the position of the guide post along the support frame;
recording the angular position of the support arm and the height of the support arm along the guide post; and
recording the position of the sensing means along the support arm.

11. A method according to claim 10, wherein the displaying step includes the steps of:
searching through the first memory for the largest number therein;
searching through the second memory for the largest number therein; and
displaying a number representing the ratio of the largest number in the first memory to the largest number in the second memory.

12. A method according to claim 10, wherein the displaying step includes the steps of:
integrating the force applied to the sensing means during the first test period by
 (i) multiplying each of the numbers stored in the first memory by the first time interval to establish a multitude of first sub-integrals, and
 (ii) adding together all of the first sub-integrals to establish a first integral;
integrating the force applied to the sensing means during the second test period by
 (i) multiplying each of the numbers stored in the second memory by the second time interval to establish a multitude of second sub-integrals, and
 (ii) adding together all of the second sub-integrals to establish a second integral; and
displaying a number representing the ratio of the first integral to the second integral.

13. Apparatus for testing the strength of muscles and muscle groups of a person, comprising:

a support stand;
a guide post;
first connecting means connecting the guide post to the support stand;
a support arm;
second connecting means connecting the support arm to the guide post, the second connecting means having a locked position, wherein the support arm is rigidly connected to the guide post, and an unlocked position, wherein the support arm is supported by the guide post for sliding movement along the guide post;
sensing means connected to the support arm to engage a body area of the person subjected to a force from a selected muscle or muscle group, and to generate an initial signal in response to the force; and
processing and display means connected to the sensing means to receive the initial signal therefrom, to process the initial signal and to produce and display a resultant signal representing said force;
wherein the support stand includes
 (i) a base,
 (ii) a left leg including upper and lower sections,
 (iii) a right leg including upper and lower sections,
 (iv) means connecting the lower sections of the left and right legs to the base for movement between a folded position, wherein said lower sections are generally parallel to the base, and an open position, wherein said lower sections extend upward from the base,
 (v) means connecting the upper section of the left leg to the lower section thereof for movement between a folded position wherein the upper section of the left leg forms an acute angle with the lower section thereof, and an open position wherein the upper section of the left leg is generally co-linear with the lower section thereof, and connecting the upper section of the right leg to the lower section thereof for movement between a folded position wherein the upper section of the right leg forms an acute angle with the lower section thereof, and an open position wherein the upper section of the right leg is generally co-linear with the lower section thereof, and
 (vi) means releasably holding the lower sections in their open position, releasably holding the upper section of the left leg in its open position, and releasably holding the upper section of the right leg in its open position.

14. Apparatus according to claim 13, wherein:
the base includes an edge, and
the apparatus further comprises at least a first wheel rotatably connected to the base and projecting over the edge of the base to facilitate rolling the base along a surface.

* * * * *